United States Patent
Liu et al.

(10) Patent No.: US 8,621,924 B2
(45) Date of Patent: Jan. 7, 2014

(54) HUMIDITY SENSING CIRCUIT WITH TEMPERATURE COMPENSATION

(75) Inventors: Te-Chung Liu, Taoyuan Hsien (TW); Yi-Hua Lee, Taoyuan Hsien (TW)

(73) Assignee: Delta Electronics, Inc., Taoyuan Hsien (TW)

( * ) Notice: Subject to any disclaimer, the term of this patent is extended or adjusted under 35 U.S.C. 154(b) by 376 days.

(21) Appl. No.: 12/958,840

(22) Filed: Dec. 2, 2010

(65) Prior Publication Data

US 2011/0138908 A1 Jun. 16, 2011

(30) Foreign Application Priority Data

Dec. 15, 2009 (TW) ................ 98142865 A

(51) Int. Cl.
*G01N 19/00* (2006.01)
(52) U.S. Cl.
USPC ...................................... 73/335.04
(58) Field of Classification Search
USPC ...................................... 73/335.04
See application file for complete search history.

(56) References Cited

U.S. PATENT DOCUMENTS

| 4,816,748 | A | * | 3/1989 | Tazawa et al. | ............... 324/694 |
| 5,531,097 | A | | 7/1996 | Tsuchida et al. | |
| 5,909,061 | A | * | 6/1999 | Sasaki et al. | ................ 307/44 |
| 7,267,002 | B2 | * | 9/2007 | Itakura et al. | ............ 73/335.03 |

FOREIGN PATENT DOCUMENTS

TW    M367535    10/2009

* cited by examiner

*Primary Examiner* — Hezron E Williams
*Assistant Examiner* — Rodney T Frank
(74) *Attorney, Agent, or Firm* — Muncy, Geissler, Olds & Lowe, PLLC

(57) ABSTRACT

A humidity sensing circuit with temperature compensation includes a wave producing module, a phase processing module, a sensing module and a detecting module. The wave producing module outputs a wave signal. The phase processing module outputs an oscillatory wave and an invert oscillatory wave according to the wave signal. The sensing module has a temperature sensor and a humidity sensor which are connected in series. The temperature sensor and the humidity sensor respectively receive the oscillatory wave and the invert oscillatory wave. The sensing module outputs a parameter signal according to the oscillatory wave and the invert oscillatory wave. The detecting module outputs a detection signal according to the parameter signal. Hence, the humidity sensing circuit with temperature compensation senses the temperature and humidity by the simple circuit design. Moreover, it is feasible for circuit design and application.

18 Claims, 4 Drawing Sheets

HUMIDITY SENSING CIRCUIT WITH TEMPERATURE COMPENSATION

CROSS REFERENCE TO RELATED APPLICATIONS

This Non-provisional application claims priority under 35 U.S.C. §119(a) on Patent Application No(s). 098142865 filed in Taiwan, Republic of China on Dec. 15, 2009, the entire contents of which are hereby incorporated by reference.

BACKGROUND OF THE INVENTION

1. Field of Invention

The present invention relates to a sensing circuit and, in particular, to a humidity sensing circuit with temperature compensation.

2. Related Art

FIG. 1 is a schematic diagram of a conventional temperature-humidity sensing circuit 1, which includes a humidity sensing unit 11, a temperature sensing unit 12, two analog-to-digital converters (A/D converters) 13 and 14, and a detecting unit 15. The humidity sensing unit 11 has an operation amplifier 111, a plurality of resisters R, and a plurality of sensors O. In the humidity sensing unit 11, the humidity signal detected by the sensor O is processed by the resistors R and operation amplifier 111 so as to output an analog signal S1 with respective to the humidity. Then, the analog-to-digital converter 13 converts the analog signal S1 to a digital signal S2. Meanwhile, the temperature sensing unit 12 measures the temperature to correspondingly output an analog signal S3, and then the analog-to-digital converter 14 converts the analog signal S3 to a digital signal S4. The detecting unit 15, which includes a comparison table and a microprocessor, receives the digital signals S2 and S4 with respective to the humidity and temperature respectively. The microprocessor outputs a suitable control signal S5 based on the comparison table in view of the digital signals S2 and S4.

The conventional temperature-humidity sensing circuit must detect the current temperature and humidity respectively, and then output the control signal through the detecting unit, so that two analog-to-digital converters are necessary. However, the analog-to-digital converter is a large and complicated circuit for converting the detected analog signal to a digital signal, and the digital signals with respective to the temperature and humidity must be integrated by the microprocessor. Accordingly, the entire temperature-humidity sensing circuit has a very complex circuit and involves large amount of electronic components, so that the manufacturing cost as well as the total volume is increased. Therefore, it is an important aspect of the present invention to provide a humidity sensing circuit with temperature compensation that has simple circuit design for detecting both temperature and humidity, thereby being suitable for further circuit design and application.

SUMMARY OF THE INVENTION

In view of the foregoing, it is an aspect of the present invention to provide a humidity sensing circuit with temperature compensation that has simple circuit design for detecting both temperature and humidity, thereby being suitable for further circuit design and application.

To achieve the above-mentioned aspect, the present invention discloses a humidity sensing circuit with temperature compensation including a wave producing module, a phase processing module, a sensing module and a detecting module. The wave producing module is capable of outputting a wave signal. The phase processing module is capable of outputting an oscillatory wave and an invert oscillatory wave according to the wave signal. The sensing module has a temperature sensor and a humidity sensor, which are connected and respectively receive the oscillatory wave and the invert oscillatory wave. The sensing module is capable of outputting a parameter signal according to the oscillatory wave and the invert oscillatory wave. The detecting module is capable of outputting a detection signal according to the parameter signal.

In one aspect of the invention, the wave producing module includes an operation amplifier, a first resistor, a second resistor, a third resistor, a fourth resistor, and a capacitor.

In one aspect of the invention, the phase processing module includes two Schmitt trigger circuits.

In one aspect of the invention, the phase processing module includes a first comparator and a second comparator.

In one aspect of the invention, the humidity sensing circuit further includes a reference signal producing module electrically connected with a negative input terminal of the first comparator and a positive input terminal of the second comparator, respectively.

In one aspect of the invention, the wave producing module is electrically connected with a positive input terminal of the first comparator and a negative input terminal of the second comparator, respectively.

In one aspect of the invention, the phase processing module further includes two amplifiers electrically connected with the first comparator and the second comparator, respectively.

In one aspect of the invention, the phase processing module further includes two attenuators electrically connected with the first comparator and the second comparator, respectively.

In one aspect of the invention, the amplitudes of the oscillatory wave and the invert oscillatory wave are the same.

In one aspect of the invention, the phases of the oscillatory wave and the invert oscillatory wave are inverted.

In one aspect of the invention, each of the oscillatory wave and the invert oscillatory wave is a square wave.

In one aspect of the invention, the detecting module includes a switch unit and a detecting unit. The switch unit includes a switch element, and one end of the switch element is electrically connected with the detecting unit.

In one aspect of the invention, the detecting unit includes an operation amplifier, a seventh resistor, an eighth resistor, a ninth resistor, a capacitor, and a diode.

As mentioned above, the humidity sensing circuit with temperature compensation of the invention has a phase processing module for outputting an oscillatory wave and an invert oscillatory wave, which have the same amplitudes and inverted phases. The sensing module receives the oscillatory wave and the invert oscillatory wave, and then the temperature sensor and the humidity sensor outputs a parameter signal according to the oscillatory wave and the invert oscillatory wave. Finally, the detecting module outputs a detection signal according to the parameter signal. Thus, the humidity sensing circuit with temperature compensation of the invention can sense the temperature and humidity simultaneously with simple circuit design, so that the feasibility of circuit design and application is achieved.

BRIEF DESCRIPTION OF THE DRAWINGS

The present invention will become more fully understood from the subsequent detailed description and accompanying drawings, which are given by way of illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1:
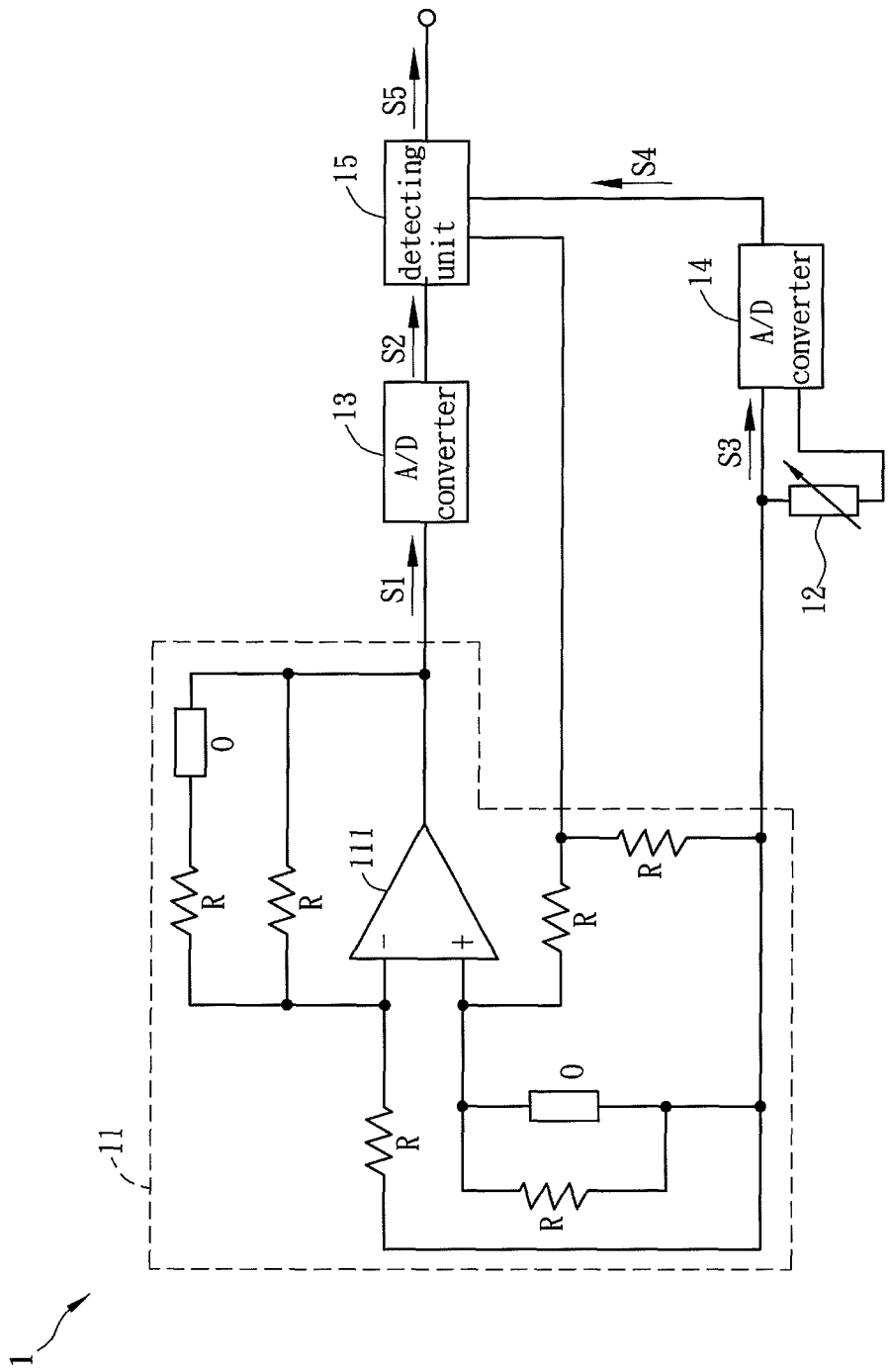
FIG. 1 is a schematic diagram showing a conventional temperature-humidity sensing circuit.
Figure 2:
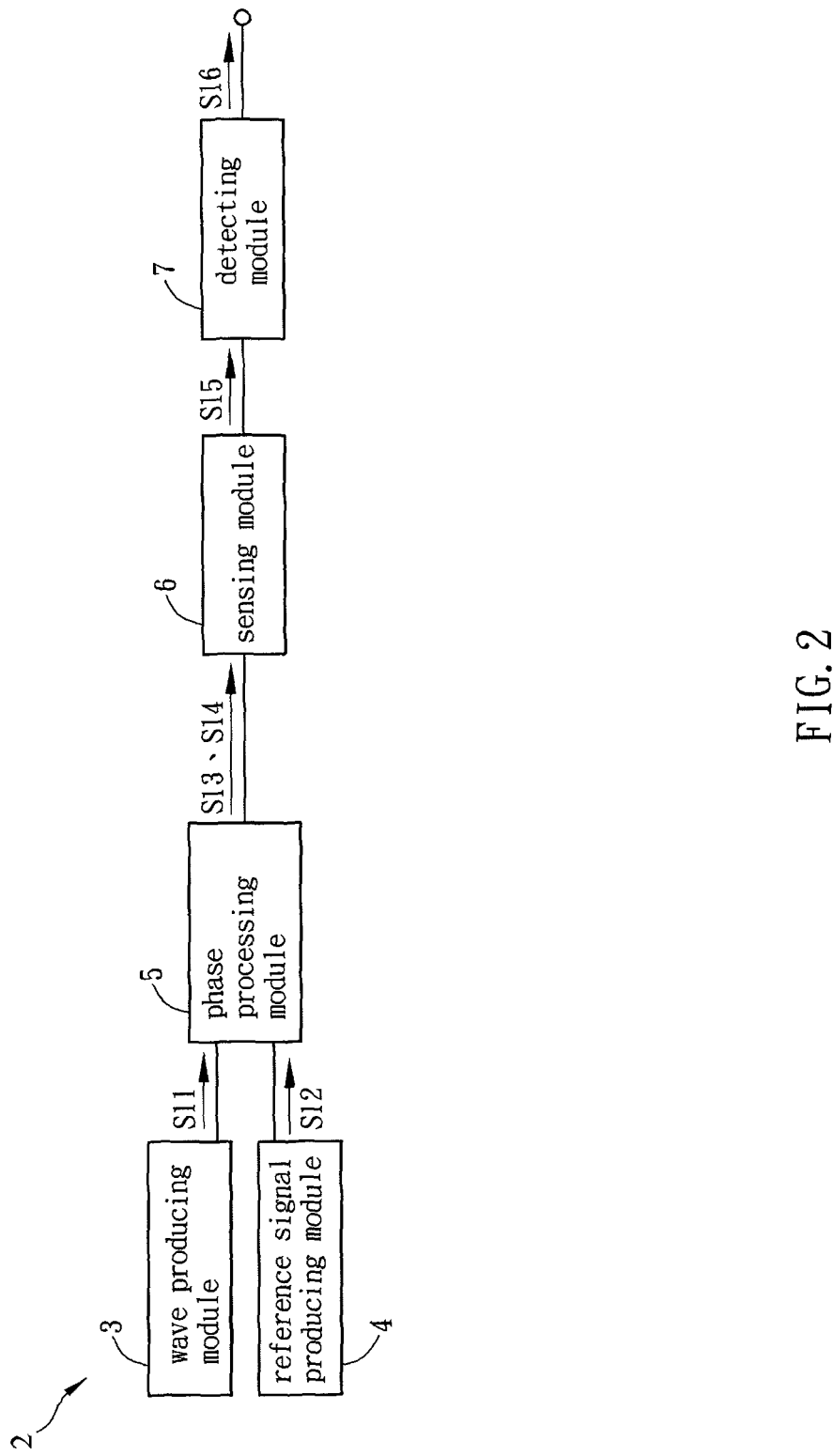
FIG. 2 is a schematic diagram of a humidity sensing circuit with temperature compensation according to an embodiment of the invention.

FIG. 2 is a schematic diagram of a humidity sensing circuit with temperature compensation according to an embodiment of the invention. As shown in FIG. 2, the humidity sensing circuit 2 includes a wave producing module 3, a reference signal producing module 4, a phase processing module 5, a sensing module 6, and a detecting module 7.

The wave producing module 3 outputs a wave signal S11, and the reference signal producing module 4 outputs a reference signal S12. The phase processing module 5 is electrically connected with the wave producing module 3 and the reference signal producing module 4 for receiving the wave signal S11 and the reference signal S12, and then outputs an oscillatory wave S13 and an invert oscillatory wave S14 according to the wave signal S11 and the reference signal S12. The sensing module 6 is electrically connected with the phase processing module 5 for receiving the oscillatory wave S13 and the invert oscillatory wave S14, and then outputs a parameter signal S15 according to the oscillatory wave S13 and the invert oscillatory wave S14. The detecting module 7 outputs a detection signal S16 according to the parameter signal S15.

Figure 3:
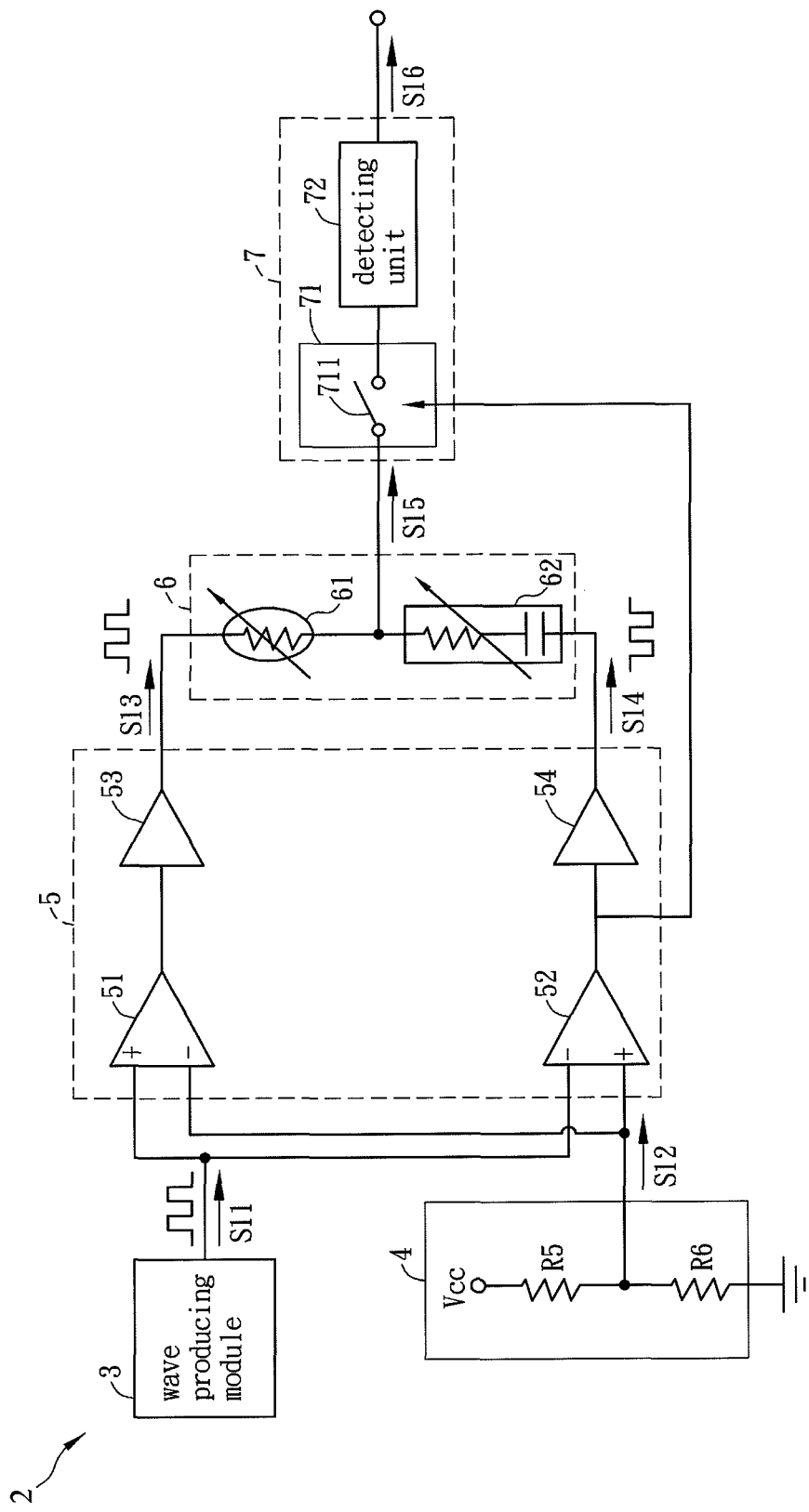
FIG. 3 is a circuit diagram of the humidity sensing circuit with temperature compensation according to the embodiment of the invention.
Figure 4:
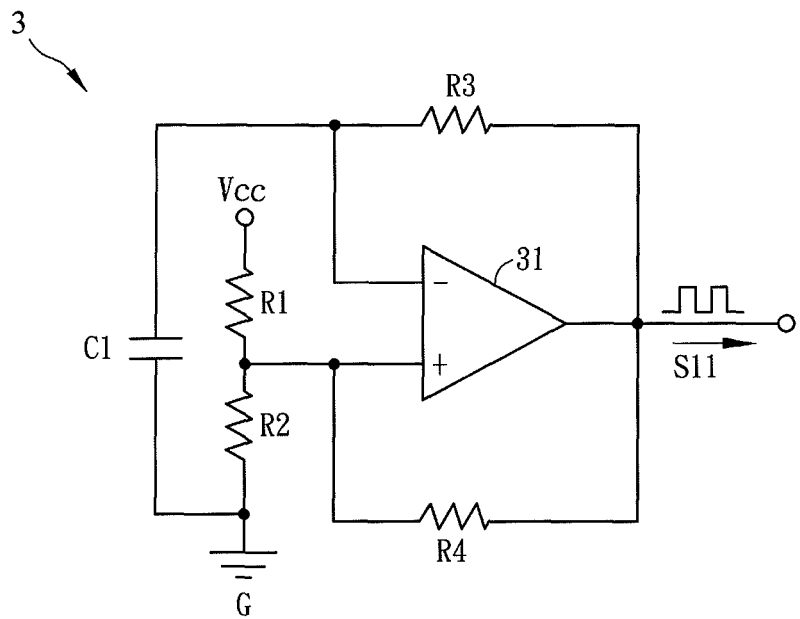
FIG. 4 is a schematic diagram of a wave producing module according to the embodiment of the invention.

FIG. 3 is a circuit diagram of the humidity sensing circuit with temperature compensation according to the embodiment of the invention, and FIG. 4 is a schematic diagram of a wave producing module according to the embodiment of the invention. Referring to FIGS. 3 and 4, the wave producing module 3 includes an operation amplifier 31, a first resistor R1, a second resistor R2, a third resistor R3, a fourth resistor R4, and a capacitor C1. One end of the first resistor R1 receives a power signal Vcc, and the other end thereof is electrically connected with a positive input terminal of the operation amplifier 31. One end of the second resistor R2 is electrically connected with the positive input terminal of the operation amplifier 31, and the other end thereof is electrically connected with a ground G. One end of the third resistor R3 is electrically connected with a negative input terminal of the operation amplifier 31, and the other end thereof is connected with an output terminal of the operation amplifier 31. One end of the fourth resistor R4 is electrically connected with the positive input terminal of the operation amplifier 31, and the other end thereof is connected with the output terminal of the operation amplifier 31. One end of the capacitor C1 is electrically connected with a negative input terminal of the operation amplifier 31, and the other end thereof is electrically connected with the ground G. The output terminal of the wave producing module 3 outputs a wave signal S11, which is a square wave for example.

Referring to FIG. 3, the reference signal producing module 4 includes a fifth resistor R5 and a sixth resistor R6. One end of the fifth resistor R5 receives a power signal Vcc, and the other end thereof is electrically connected with one end of the sixth resistor R6. The other end of the sixth resistor R6 is electrically connected with the ground G. Thus, the power signal Vcc can be divided by the fifth resistor R5 and the sixth resistor R6, and then a reference signal S12 can be outputted through the connection of the fifth resistor R5 and the sixth resistor R6.

The phase processing module 5 includes a first comparator 51 and a second comparator 52, which are electrically connected with the wave producing module 3 and the reference signal producing module 4, respectively. The wave producing module 3 outputs the wave signal S11 to the positive input terminal of the first comparator 51 and the negative input terminal of the second comparator 52. The reference signal producing module 4 outputs the reference signal S12 to the negative input terminal of the first comparator 51 and the positive input terminal of the second comparator 52. Consequently, the output signals of the first comparator 51 and the second comparator 52 can have the same amplitude and inverted phases.

Alternatively, the phase processing module 5 may have two Schmitt trigger circuits (not shown) for replacing the above-mentioned first comparator 51 and the second comparator 52. The Schmitt trigger circuits are electrically connected with the wave producing module 3 and the reference signal producing module 4. One of the Schmitt trigger circuits is an inverting Schmitt trigger circuit, and the other one is a non-inverting Schmitt trigger circuit.

In this embodiment, the phase processing module 5 may further include two amplifiers such as a first amplifier 53 and a second amplifier 54. The first amplifier 53 is electrically connected with the first comparator 51, and the second amplifier 54 is electrically connected with the second comparator 52. Thus, the first amplifier 53 and the second amplifier 54 can amplify the signals outputted from the first comparator 51 and the second comparator 52, and then the phase processing module 5 can output the oscillatory wave S13 and the invert oscillatory wave S14 according to the amplified signals. Herein, the amplitudes of the oscillatory wave S13 and the invert oscillatory wave S14 are the same, and the phases thereof are inverted. In other words, when the oscillatory wave S13 is in a positive phase, the invert oscillatory wave S14 is in a negative phase; otherwise, when the oscillatory wave S13 is in a negative phase, the invert oscillatory wave S14 is in a positive phase. For example, the oscillatory wave S13 and the invert oscillatory wave S14 of the embodiment are both a square wave.

Alternatively, the phase processing module 5 of the embodiment may further include two attenuators (not shown) to replacing the above-mentioned amplifiers. The attenuators are electrically connected with the first comparator 51 and the second comparator 52, respectively, for attenuating the signals outputted from the first comparator 51 and the second comparator 52. To be noted, either the amplifiers or the attenuators can be used depending on the overall design, and may be influenced by the level of the power source and the durability of the electronic components such as the temperature sensor and the humidity sensor.

The sensing module 6 has a temperature sensor 61 and a humidity sensor 62 connected in series. One end of the temperature sensor 61 is connected to one end of the humidity sensor 62, and the other ends of the temperature sensor 61 and the humidity sensor 62 respectively receive the oscillatory wave S13 and the invert oscillatory wave S14. The impendence of the temperature sensor 61 and the impendence of the humidity sensor 62 can be various according to the environment temperature and humidity, respectively. Moreover, the oscillatory wave S13 and the invert oscillatory wave S14 have the same amplitude and different phases, so that there are certain voltage differences between two ends of the temperature sensor 61 and the humidity sensor 62. Accordingly, the temperature sensor 61 and the humidity sensor 62 can generate divided voltages according to the oscillatory wave S13 and the invert oscillatory wave S14, and a reference signal S15 can be outputted from the connection of the temperature sensor 61 and the humidity sensor 62. To be noted, since the oscillatory wave S13 and the invert oscillatory wave S14 have symmetrical waves, they may approach the alternate signal, so that the sensing module 6 can precisely response the sensed values and the temperature sensor 61 and the humidity sensor 62 can be protected.

Figure 5:
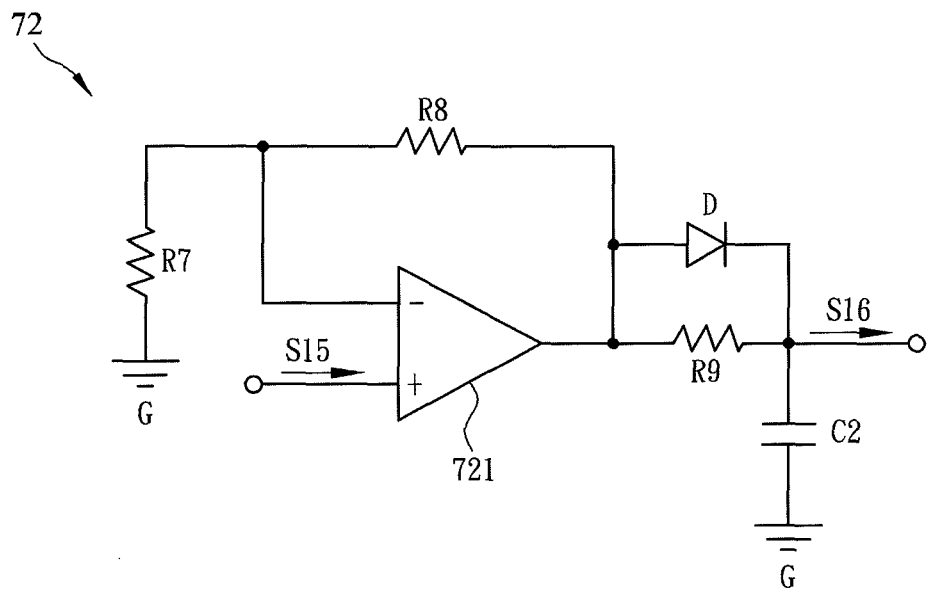
FIG. 5 is a schematic diagram of a detecting unit according to the embodiment of the invention.

The detecting module 7 includes a switch unit 71 and a detecting unit 72. The switch unit 71 has a switch element 711 having one end electrically connected to the connection of the temperature sensor 61 and the humidity sensor 62 and the other end electrically connected with the detecting unit 72. In this embodiment, the switch element 711 is turned ON/OFF according to a signal outputted from the second comparator 52. FIG. 5 is a schematic diagram of a detecting unit 72 according to the embodiment of the invention. With reference to FIGS. 3 and 5, the detecting unit 72 includes an operation amplifier 721, a seventh resistor R7, an eighth resistor R8, a ninth resistor R9, a diode D, and a capacitor C2. The positive input terminal of the operation amplifier 721 receives the reference signal S15 from the switch element 711. One end of the seventh resistor R7 is electrically connected with a negative input terminal of the operation amplifier 721, and the other end thereof is connected to a ground G. One end of the eighth resistor R8 is electrically connected with a negative input terminal of the operation amplifier 721, and the other end thereof is electrically connected with an output terminal of the operation amplifier 721. One end of the ninth resistor R9 is electrically connected with an output terminal of the operation amplifier 721, and the other end thereof is connected with the capacitor C2. The diode D is connected with the ninth resistor R9 in parallel. That is, the diode D is electrically connected to the output terminal of the operation amplifier 721 and the capacitor C2. The end of the capacitor C is electrically connected with the ground G. In this embodiment, the capacitor C2 and the ninth resistor R9 together form an integrator. The operation amplifier 721 of the detecting unit 72 receives the reference signal S15 and amplifies the reference signal S15. Then, the detecting module 7 outputs a detection signal S16 according to a humidity measuring value with respective to the amplified reference signal S15. Herein, the detection signal S16 can be directly used as a driving signal of a load, such as a fan or a motor, or provided to the microprocessor to read the humidity value.

To sum up, the humidity sensing circuit with temperature compensation of the invention has a phase processing module for outputting an oscillatory wave and an invert oscillatory wave, which have the same amplitudes and inverted phases. The sensing module receives the oscillatory wave and the invert oscillatory wave, and then the temperature sensor and the humidity sensor outputs a parameter signal according to the oscillatory wave and the invert oscillatory wave. In the invention, the oscillatory wave and the invert oscillatory wave may approach the alternate signal, so that the temperature sensor and the humidity sensor can precisely response the sensed values. Finally, the detecting module outputs a detection signal according to the parameter signal. In one embodiment of the invention, the detection signal can be directly used as a driving signal of a load or provided to the microprocessor to read the humidity value. For example, the temperature sensor and the humidity sensor are connected in series for achieving the temperature compensation of the outputted humidity signal, so that the reference signal has already involved the humidity signal with temperature compensation. Thus, the complex components for the conventional comparison table and the related determine actions may not be necessary. Thus, the humidity sensing circuit with temperature compensation of the invention can sense the temperature and humidity simultaneously with simple circuit design. Moreover, the detection signal outputted from the detecting module may be directly used as a driving signal of a load, and it is feasible for circuit design and application.

Although the present invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the present invention.

What is claimed is:

1. A humidity sensing circuit with temperature compensation, comprising:
    a wave producing module, capable of outputting a wave signal, wherein the wave producing module comprises:
    an operation amplifier;
    a first resistor having one end for receiving a power signal and the other end electrically connected with a positive input terminal of the operation amplifier;
    a second resistor having one end electrically connected with the positive input terminal of the operation amplifier and the other end grounded;
    a third resistor having one end electrically connected with a negative input terminal of the operation amplifier and the other end connected with an output terminal of the operation amplifier;
    a fourth resistor having one end electrically connected with the positive input terminal of the operation amplifier and the other end connected with the output terminal of the operation amplifier; and
    a capacitor having one end electrically connected with a negative input terminal of the operation amplifier and the other end grounded;
    a phase processing module, capable of receiving the wave signal and outputting an oscillatory wave and an invert oscillatory wave according to the wave signal;
    a sensing module having a temperature sensor and a humidity sensor connected in series, wherein the temperature sensor and the humidity sensor respectively receive the oscillatory wave and the invert oscillatory wave, and the sensing module is capable of outputting a parameter signal according to the oscillatory wave and the invert oscillatory wave; and
    a detecting module, capable of outputting a detection signal according to the parameter signal.

2. The humidity sensing circuit with temperature compensation according to claim 1, wherein the wave signal is a square wave signal.

3. A humidity sensing circuit with temperature compensation, comprising:
    a wave producing module, capable of outputting a wave signal;

a phase processing module, capable of receiving the wave signal and outputting an oscillatory wave and an invert oscillatory wave according to the wave signal;

a sensing module having a temperature sensor and a humidity sensor connected in series, wherein the temperature sensor and the humidity sensor respectively receive the oscillatory wave and the invert oscillatory wave, and the sensing module is capable of outputting a parameter signal according to the oscillatory wave and the invert oscillatory wave; and a detecting module, capable of outputting a detection signal according to the parameter signal, wherein the phase processing module comprises two Schmitt trigger circuits.

4. The humidity sensing circuit with temperature compensation according to claim 3, wherein one of the Schmitt trigger circuits is an inverting Schmitt trigger circuit, and the other one of the Schmitt trigger circuits is a non-inverting Schmitt trigger circuit.

5. The humidity sensing circuit with temperature compensation according to claim 1 wherein the phase processing module comprises a first comparator and a second comparator.

6. A humidity sensing circuit with temperature compensation, comprising:

a wave producing module, capable of outputting a wave signal;

a phase processing module, capable of receiving the wave signal and outputting an oscillatory wave and an invert oscillatory wave according to the wave signal, wherein the phase processing module comprises a first comparator and a second comparator;

a sensing module having a temperature sensor and a humidity sensor connected in series, wherein the temperature sensor and the humidity sensor respectively receive the oscillatory wave and the invert oscillatory wave, and the sensing module is capable of outputting a parameter signal according to the oscillatory wave and the invert oscillatory wave;

a detecting module, capable of outputting a detection signal according to the parameter signal; and a reference signal producing module electrically connected with a negative input terminal of the first comparator and a positive input terminal of the second comparator, respectively.

7. The humidity sensing circuit with temperature compensation according to claim 6, wherein the reference signal producing module comprises a fifth resistor and a sixth resistor, one end of the sixth resistor is electrically connected with the fifth resistor, and the other end of the sixth resistor is grounded.

8. The humidity sensing circuit with temperature compensation according to claim 5, wherein the wave producing module is electrically connected with a positive input terminal of the first comparator and a negative input terminal of the second comparator, respectively.

9. A humidity sensing circuit with temperature compensation, comprising:

a wave producing module, capable of outputting a wave signal;

a phase processing module, capable of receiving the wave signal and outputting an oscillatory wave and an invert oscillatory wave according to the wave signal;

a sensing module having a temperature sensor and a humidity sensor connected in series, wherein the temperature sensor and the humidity sensor respectively receive the oscillatory wave and the invert oscillatory wave, and the sensing module is capable of outputting a parameter signal according to the oscillatory wave and the invert oscillatory wave; and a detecting module, capable of outputting a detection signal according to the parameter signal, wherein the phase processing module comprises a first comparator and a second comparator, and the phase processing module further comprises two amplifiers electrically connected with the first comparator and the second comparator, respectively.

10. A humidity sensing circuit with temperature compensation, comprising:

a wave producing module, capable of outputting a wave signal;

a phase processing module, capable of receiving the wave signal and outputting an oscillatory wave and an invert oscillatory wave according to the wave signal;

a sensing module having a temperature sensor and a humidity sensor connected in series, wherein the temperature sensor and the humidity sensor respectively receive the oscillatory wave and the invert oscillatory wave, and the sensing module is capable of outputting a parameter signal according to the oscillatory wave and the invert oscillatory wave; and a detecting module, capable of outputting signal according to the parameter signal, wherein the phase processing module comprises a first comparator and a second comparator, and the phase processing module further comprises two attenuators electrically connected with the first comparator and the second comparator, respectively.

11. The humidity sensing circuit with temperature compensation according to claim 1, wherein the amplitudes of the oscillatory wave and the invert oscillatory wave are the same.

12. The humidity sensing circuit with temperature compensation according to claim 11, wherein the phases of the oscillatory wave and the invert oscillatory wave are inverted.

13. The humidity sensing circuit with temperature compensation according to claim 1, wherein the oscillatory wave is a square wave.

14. The humidity sensing circuit with temperature compensation according to claim 1, wherein the invert oscillatory wave is a square wave.

15. A humidity sensing circuit with temperature compensation, comprising:

a wave producing module, capable of outputting a wave signal;

a phase processing module, capable of receiving the wave signal and outputting an oscillatory wave and an invert oscillatory wave according to the wave signal;

a sensing module having a temperature sensor and a humidity sensor connected in series, wherein the temperature sensor and the humidity sensor respectively receive the oscillatory wave and the invert oscillatory wave, and the sensing module is capable of outputting a parameter signal according to the oscillatory wave and the invert oscillatory wave; and a detecting module, capable of outputting a detection signal according to the parameter signal, wherein the phase processing module comprises a first comparator and a second comparator, and the detecting module comprises:

a switch unit comprising a switch element; and a detecting unit electrically connected with one end of the switch element.

16. The humidity sensing circuit with temperature compensation according to claim 15, wherein the switch element is turned ON/OFF according to a signal outputted from the second comparator.

17. The humidity sensing circuit with temperature compensation according to claim 15, wherein the detecting unit comprises:
- an operation amplifier, wherein a positive input terminal of the operation amplifier receives the reference signal;
- a seventh resistor having one end electrically connected with a negative input terminal of the operation amplifier and the other end grounded;
- an eighth resistor having one end electrically connected with a negative input terminal of the operation amplifier and the other end electrically connected with an output terminal of the operation amplifier;
- a ninth resistor having one end electrically connected with an output terminal of the operation amplifier;
- a diode connected with the ninth resistor in parallel; and
- a capacitor having one end electrically connected with the ninth resistor and the other end grounded.

18. The humidity sensing circuit with temperature compensation according to claim 17, wherein the capacitor and the ninth resistor form an integrator.

\* \* \* \* \*